United States Patent
Cappello

(10) Patent No.: US 7,803,357 B2
(45) Date of Patent: Sep. 28, 2010

(54) TOPICAL AND TRANSDERMAL TREATMENTS USING UREA FORMULATION

(76) Inventor: John V Cappello, Valley Forge Towers, 20104 Valley Forge Cir., King of Prussia, PA (US) 19406

( * ) Notice: Subject to any disclaimer, the term of this patent is extended or adjusted under 35 U.S.C. 154(b) by 16 days.

(21) Appl. No.: 12/290,744

(22) Filed: Nov. 3, 2008

(65) Prior Publication Data

US 2009/0069359 A1 Mar. 12, 2009

Related U.S. Application Data

(63) Continuation-in-part of application No. 11/590,037, filed on Oct. 30, 2006, now Pat. No. 7,445,783.

(51) Int. Cl.
*A01N 61/00* (2006.01)
*A61Q 9/00* (2006.01)

(52) U.S. Cl. .......................... 424/70.1; 514/1; 514/880

(58) Field of Classification Search ........................ None
See application file for complete search history.

(56) References Cited

U.S. PATENT DOCUMENTS

| 4,309,989 | A | * | 1/1982 | Fahim | ........................... 601/2 |
| 5,643,584 | A | * | 7/1997 | Farng et al. | ................ 424/401 |
| 5,654,337 | A | * | 8/1997 | Roentsch et al. | ............ 514/570 |
| 7,445,783 | B2 | * | 11/2008 | Cappello | ................ 424/184.1 |

OTHER PUBLICATIONS

Kim et al (Journal of Plastic, Reconstructive & Aesthetic Surgery vol. 62, No. 7, pp. 906-913, 2009).*

* cited by examiner

*Primary Examiner*—Mark Navarro
(74) *Attorney, Agent, or Firm*—Lawrence J. Shurupoff

(57) ABSTRACT

Various medical conditions, some previously treated by injection or surgery, are effectively treated by a topical application of a composition of urea and a chemotherapeutic agent. Such agents include sclerosing agents, vasodilators, botulinum toxin and minoxidil. Conditions as diverse as spider veins, erectile dysfunction, facial wrinkles, hair loss and baldness can be effectively treated with the compositions.

3 Claims, No Drawings

TOPICAL AND TRANSDERMAL TREATMENTS USING UREA FORMULATION

CROSS REFERENCE TO RELATED APPLICATIONS

This application is a continuation-in-part application of application Ser. No. 11/590,037 filed Oct. 30, 2006 titled Topical and Transdermal Treatments Using Urea. This application claims the benefit and priority of application Ser. No. 11/590,037 which is incorporated by reference herein in its entirely.

BACKGROUND

The present invention relates in general to compositions containing urea, and to methods of treating medical conditions using such compositions.

SUMMARY

Urea, by nature of its keratolytic action and humectant effect appears to prepare the substrate of the skin for ideal topical penetration of chemotherapeutic agents, and particularly those agents described herein. This action is believed to be effective with other chemotherapeutic agents in a broader sense. The complete mechanism of action of these agents with urea is not fully understood. What is known is that other topical formulations tried without urea were not effective or as effective as those used in combination with urea in topically treating various medical conditions.

An effective urea concentration for its topical use in combination with other chemotherapeutic agents is believed to be in the range of 10% to 40% by weight of the formulation. One specific urea-containing formulation used was an over-the-counter topical skin cream sold under the brand Dermal Therapy and manufactured by Bayer. The Dermal Therapy formulation contains deionized water, urea USP, propylene glycol, triethanolamineamine, hydrogenated polyisobutene, isopropyl myristate, lactic acid, cetyl alcohol, GMS PEG stearate, malic acid, emulsifying wax, silk protein amino acid, idmadazolidinyl urea, carbamer 941, sorbic acid, tetra sodium EDTA, and quaternium 15.

This Dermal Therapy product formulation will be referred to herein as "the base" to which other chemotherapeutic agents are combined to form a topical therapeutic skin cream. Of course, other skin creams, lotions or oils containing urea can also be effectively used. It is only the urea in the Dermal Therapy base which is considered necessary to carry out the present invention. The ingredients other than urea in Dermal Therapy are not necessary to achieve the results described in detail below.

Other bases without urea have been tried without success. For example, petroleum jelly and other cosmetic creams without urea were tried to treat the conditions noted below without success. Only when urea was included in the formulation were any positive results achieved. Any suitable carrier for applying urea and a therapeutic agent to the skin can be used in accordance with the invention.

Various other objects, features and attendant advantages of the present invention will be more fully appreciated as the same becomes better understood from the following detailed description.

DETAILED DESCRIPTION

A particularly effective use of urea has been found in the topical treatment of spider veins and superficial varicosities. These are common skin problems occurring on the legs and on the face as telangectasias. As such, they are deemed unsightly in general by those who have them.

By mixing a sclerosing agent to the base (Dermal Therapy) in a formulation containing 1to 10% by weight of such an agent, spider veins disappear or become progressively better (less visible) after 90 days of treatment. The formulation was used at least two times per day, at least once in the morning and at least once in the evening. The specific agent used was sodium morrhuate in an amount of 5% by weight. However, sodium morrurate can be used effectively in the range of 1% to 10% by weight. By extension, other such sclerosing agents, or mixtures thereof, including ethyl morrhuate, Vitamin K, hypertonic saline, dextrose solution and any other known injectible sclerosing agents should also work effectively in such treatment, both topically and transdermally.

Three female patients with spider veins covering 1 to 3 square inches on their anterior thighs were topically administered 5% by weight of sodium morrhuate in the base. Within 90 days, all three patients were completely resolved of any spider vein appearances.

In other examples, formulations with 1 cc to 10 cc of sodium mourrhuate in a one ounce vanishing cream base (the base) were given to subjects to apply to their spider veins and small varicosites on a daily basis. In the half dozen subjects tested, the spider veins and small varicosities were eliminated. Results were obtained in 30 to 90 days, on average, and may vary based upon compliance of using the composition daily to the affected sites.

Another application of urea formulations is in the topical treatment of erectile dysfunction. There are two major physical causes of erectile dysfunction. One cause is a decrease in nitric oxide and the other is a decrease of circulation to the penis and corpus cavernous. If this circulation is hampered, the effect of exogenous or endogenous nitric oxide production will be diminished.

By mixing a vasodilator such as menthol or eucalyptol, or a mixture thereof, to the base in a formulation containing 0.04% to 1% by weight of such a vasodilator, or mixture of vasodilators, improved erections were obtained within 90 days without the addition of nitric oxide enhancing agents. The vasodilator formulation was used at least two times per day, morning and evening, and applied generously over the shaft of the penis.

Three males who had experienced erectile problems relating to the inability to enter the vagina in a hardened state reported gradual improvement to the stage of again being able to experience intravaginal orgasm. This improvement occurred over a 90 day period of application. It is likely that ongoing use of the treatment may be needed, since the salubrious effect of the topical composition does not appear to be a permanent one of blood vessel dilation.

By extension, other vasodilators such as propranolol, and others in its class of beta blockers as well as any known pharmaceutical which is known to produce vasodilation can be added to a base containing urea. This would also include the addition of calcium channel blockers and nitrates to the base.

The use of urea in combination with other topical agents has proved useful in the treatment of Peyronie's disease. This condition is a result of blood vessel plaquing in the penile shaft, as well as concomitant faulty blood circulation.

A formulation using 0.05% to 5.0% by weight of propranolol in the previously mentioned base (Dermal Therapy) was used on an individual with Peyronie's disease so severe as not to permit penile entry in the vagina. The specific formulation contained 0.5% propranolol. Within 90 days of using the formulation in the morning and at bedtime, the subject, with a downward "C" penile arc, gradually attained a straightened penis over 90 days, thereby permitting vaginal entry. Once again, it is believed that any known pharmaceutical with a vasodilation effect would produce similar results with the base.

Another application of urea base formulations is effective in treating facial wrinkles. Botox, (botulinum toxina) is known to produce an effect of decreasing wrinkles through muscle relaxation. However, until now, Botox only has worked by injection. Retin A produces a similar decrease in skin aging through a different mechanism over a longer period of time by causing desquamation, thereby permitting other topicals to enter the dermis. Retin A along with the base effectively permits entry of Botox into and through the skin.

The use of Botox, Retin A and the base creates a formulation capable of safely, and in a low dose, dramatically decreasing facial wrinkles around the eyes and mouth.

Formulations containing as low as 0.05% by weight of Botox and 0.05% by weight Retin A mixed within the base have been used successfully in 12 subjects. The wrinkle reducing effect occurs over a 72 hour period and lasts up to one week. Such a product is used for nighttime application over wrinkled areas on an as—needed basis. While higher concentrations may be considered, it is best to err on the side of least possible harm by using lower concentrations of Botox and Retin A.

The topical application of known pharmaceutical agents can cause an improvement in a medical condition. The use of the base containing urea USP augments and facilitates the medical improvement. Urea appreas to enhance and facilitate transport of chemotherapeutic agents through the skin.

Another application of urea base formulations is effective in treating hair loss and baldness. Minoxidil is known to produce hair growth. A topical solution that contains 2% to 5% minoxidil has been used to treat baldness and hair loss and has been marketed under the brand name Rogaine in the U.S.

Treatment with Rogaine for women typically includes the application of a 2% weight concentration solution of minoxidil, whereas treatments with Rogaine for men typically applied a 5% concentration solution of minoxidil.

In order to increase the effectiveness of minoxidil, the scalp to be treated may be washed or rinsed with a steroid solution to make the scalp as penetrable as possible for the transdermal absorption and passage of minoxidil. While virtually any of the steroids listed below can be used for this washing application, one liquid ounce of a 0.02% solution of betamethasone added to one quart of warm water applied to the scalp as a final rinse after shampooing the scalp will condition the scalp to be particularly penetrable by minoxidil. In one embodiment, only betamethosone is used to condition the scalp prior to the application of minoxidil.

In one field test of 17 patients, a 5% solution of betamethasone was applied to the scalps of 10 men and 7 women prior to daily application of minoxidil. In each case, new hair growth began gradually after 30 days of treatment.

The absorption of minoxidil into the scalp can be further enhanced with the topical application of urea to the scalp. Urea softens and conditions the scalp for increased penetration of minoxidil into and through the scalp. Urea also increases the effectiveness and absorption of minoxidil and any other ingredients applied to the scalp along with minoxidil. In addition, urea has the ability to function as a pomade for hair styling purposes.

A combination of urea and minoxidil can be formulated as a topical liquid or cream. In one embodiment, urea in the amount of 10% to 40% by weight can be combined with 1% to 5% by weight of minoxidil in a topical skin cream base. This formulation can use urea in the form of the Dermal Therapy base noted above, or in any other form that can be applied topically. The application of a steroid prewash to the scalp, such as the bethamethasone prewash noted above, can further enhance the effectiveness of a subsequent application a urea and minoxidil formulation such that greater amounts of minoxidil are absorbed into the scalp than by using the urea and minoxidil formulation alone.

The use of a steroid in combination with a urea and minoxidil formulation, either as an integral component of the formulation, i.e., admixed with the urea and minoxidil, or applied separately as a scalp prewash, acts as a skin cleansing agent and as an anti-inflammatory agent. Any steroid applied to the scalp to condition the scalp for absorption of minoxidil can be provided in a prewash solution or directly added to the urea and minoxidil formulation in a concentration of about 0.01% to 0.02% by weight, depending on the particular steroid selected for use.

An example of one effective hair restoration formulation can be provided as a topical skin cream using any conventional skin cream as a base, such as Dermal Therapy skin cream. Urea, in an amount of 10% to 40% by weight of the final or overall combined formulation is combined with minoxidil, and preferably 1% to 2% by weight of minoxidil, although up to 5% by weight of minoxidil can be used. Additional urea can be added to a Dermal Therapy cream base, or urea can be added to a skin cream base which does not include urea to achieve the 10% to 40% weight component of urea.

The hair growth formulation can further include 0.01% to 0.1% by weight of any topical steroid ranging from hydrocortisone to the bethameethasone noted above. The amount of any particular steroid added to the formulation will depend on its strength. Larger amounts of "weaker" steroids, such as hydrocortisone, will typically be added up to 0.1% by weight and smaller amounts of "stronger" steroids, such as bethamethsone will typically be added in amounts as low as 0.01% by weight.

The following seven groups of topical steroids can be used with the urea and minoxidil formulation noted above. These groups are listed in order of the strongest or most powerful (Group I) down to the weakest or least powerful (Group VII).

Topical Steroid Group I
   Clobetasol diproprionate 0.05% (Temovate)
   Betamethasone diproprionate 0.25% (Diprolene)
   Halbetasol proprionate 0.05% (Ultravate)
   Diflorasone diacetate 0.05% (Psorcon)

Topical Steroid Group II
   Fluocinonide 0.05% (Lidex)
   Halcinonide 0.05% (Halog)
   Amcinonide 0.05% (Cyclocort)
   Desoximetasone 0.25% (Topicort)

Topical Steroid Group III
   Triamcinalone acetonide 0.5% (Kenalog, Aristocort cream)
   Mometasone furoate 0.1% (Elocon ointment)
   Fluticasone proprionate 0.005% (Cutivate)
   Betamethasone disproportionate 0.05% (Liposome)

Topical Steroid Group IV
   Fluocinolone acetonide 0.01-0.2% (Synalar, Synemol, Fluonid)
   Hydrocortisone valerate 0.2% (Westcort)
   Hydrocortisone butyrate 0.1% (Locoid)
   Flurandrenolide 0.05% (Cordran)

Triamcinalone acetonide 0.1% (Kenalog, Aristocort A ointment)
Mometasone furoate 0.1% (Elocon cream, lotion)

Topical Steroid Group V
Triamcinalone acetonide 0.1% (Kenalog, Aristocort cream, lotion)
Fluticasone propionate 0.05% (Cutivate cream)
Desonide 0.05% (Tridesilon, DesOwen ointment)
Fluocinolone acetonide 0.025% (Synalar, Synemol cream)
Hydrocortisone valerate 0.2% (Westcort cream)

Topical Steroid Group VI
Prednicarbate 0.05% (Aclovate cream, ointment)
Triamcinalone acetonide 0.025% (Aristocort A cream, Kenalog lotion)
Fluocinolone acetonide 0.01% (Capex shampoo, Dermasmooth)
Desonide 0.05% (DesOwen cream, lotion)

Topical Steroid Group VII
Hydrocortisone 2.5% (Hytone cream, lotion, ointment)
Hydrocortisone 1% (Many over-the-counter brands)

To further enhance the absorption and transdermal transport of minoxidil into the skin and scalp, a skin desquamation agent such as tretinoin, also known as the brand "Retin A", can be added to the urea, minoxidil and steroid formulation noted above. Tretinoin (Retin A) can be added to the formulation in amounts as low as 0.05% by weight or greater. A skin desquamation agent such as tretinoin will remove dead skin from the underlying live skin so as to remove any barrier presented by dead or dying outer skin layers to transdermal absorption of the urea and minoxidil formulations.

It should be noted that urea and minoxidil are the preferred components of the hair growth and hair promotion formulation. The addition of any one or more ingredients to a minoxidil and urea formulation such as a topical steroid, a separate topical steroid prewash of the scalp, and/or tretinoin (Retin A) will further enhance the absorption into the skin and the concomitant effectiveness of minoxidil for promoting hair growth.

One hair growth and stimulation formulation includes 10% to 40% by weight of urea in a liquid or cream topical base, 1% to 2% of minoxidil, 0.01% to 0.1% by weight of a topical steroid, and at least 0.05% by weight of tretinoin.

It should be noted that by combining a given amount of minoxidil with urea, more minoxidil will be absorbed into the skin than would be absorbed without the use of urea. This will allow a formulator to use less minoxidil to achieve the same amount of hair growth as can be achieved with larger amounts of minoxidil used alone. Thus, prior hair growth formulations using up to 5% by weight of minoxidil can be formulated with lesser amounts of minoxidil, such as 1% to 2% as described above, and achieve virtually the same amount of hair growth as achieved with 5% minoxidil formulations. This results in a lower cost product, with less potential for side effects from minoxidil usage, as less minoxidil need be applied to achieve the same amount of hair growth. That is, less than 2% by weight of minoxidil in combination with urea can achieve satisfactory hair growth at levels lower than those previously used.

A method of using any of the urea and minoxidil formulations described above includes applying about 15 cc of the urea and minoxidil topical formulation twice daily to the area of the scalp exhibiting hair loss then massaging the formulation into the scalp with fingers, then washing hands and fingers well. This regimen should be continued twice daily as necessary to maintain hair regrowth, as hair loss may occur upon termination of use.

Other variations are within the spirit of the present invention. Thus, while the invention is susceptible to various modifications and alternative constructions, certain embodiments thereof have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

What is claimed is:

1. A composition for the topical treatment of hair loss, comprising:
   minoxidil in an amount by weight of 1% to 5%;
   urea in an amount by weight of 10% to 40%;
   hydrocortisone in an amount by weight of 0.01% to 0.1%; and
   a skin desquamation agent comprising tretinoin in an amount by weight of at least 0.05%.

2. A composition for the topical treatment of hair loss, comprising:
   minoxidil iun an amount by weight of 1% to 5%;
   urea in an amount by weight of 10% to 40%;
   a topical steroid in an amount by weight of 0.01% to 0.1%; and a skin desquamation agent comprising tretinoin in an amount by weight of at least 0.05%.

3. A method of topically treating hair loss, comprising:
   providing the composition of claim 2 and repeatedly applying said composition to a scalp.

* * * * *